(12) United States Patent
Taurino

(10) Patent No.: US 12,290,093 B2
(45) Date of Patent: May 6, 2025

(54) LIQUID NICOTINE FORMULATION COMPRISING LOW MOLAR MASS METAL SALT

(71) Applicant: Philip Morris Products S.A., Neuchatel (CH)

(72) Inventor: Irene Taurino, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 813 days.

(21) Appl. No.: 17/417,975

(22) PCT Filed: Dec. 18, 2019

(86) PCT No.: PCT/EP2019/086111
§ 371 (c)(1),
(2) Date: Jun. 24, 2021

(87) PCT Pub. No.: WO2020/136063
PCT Pub. Date: Jul. 2, 2020

(65) Prior Publication Data
US 2022/0053816 A1 Feb. 24, 2022

(30) Foreign Application Priority Data
Dec. 28, 2018 (EP) .................................. 18248177

(51) Int. Cl.
| | |
|---|---|
| A24B 15/167 | (2020.01) |
| A61K 9/00 | (2006.01) |
| A61K 31/465 | (2006.01) |
| A61K 47/02 | (2006.01) |
| A61K 47/10 | (2017.01) |

(52) U.S. Cl.
CPC ............ *A24B 15/167* (2016.11); *A61K 9/007* (2013.01); *A61K 31/465* (2013.01); *A61K 47/02* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 2017/0189388 A1* | 7/2017 | Arnold ................... | A61K 9/006 |
| 2017/0196269 A1 | 7/2017 | Bernauer et al. | |
| 2018/0199617 A1 | 7/2018 | Iodice | |
| 2018/0199618 A1* | 7/2018 | Fuisz ..................... | A24B 15/32 |
| 2018/0256560 A1 | 9/2018 | Hoppe et al. | |
| 2019/0124982 A1 | 5/2019 | Atkins et al. | |
| 2019/0297947 A1 | 10/2019 | Bessant et al. | |

FOREIGN PATENT DOCUMENTS

| | | |
|---|---|---|
| JP | 2011-509090 A | 3/2011 |
| JP | 2015-531793 A | 11/2015 |
| WO | WO 2008/069970 A2 | 6/2008 |
| WO | WO 2012/164009 A2 | 12/2012 |
| WO | WO 2017/046400 A1 | 3/2017 |
| WO | WO 2017/051181 A1 | 3/2017 |
| WO | WO 2017/089931 A1 | 6/2017 |
| WO | WO 2017/118553 A1 | 7/2017 |
| WO | WO 2017/185051 A1 | 10/2017 |
| WO | WO 2018/215481 A1 | 11/2019 |
| WO | WO 2020/141184 A1 | 7/2020 |

OTHER PUBLICATIONS

Combined Russian Office Action and Search Report issued May 22, 2023 in Russian Patent Application No. 2021122231/04 (with English Translation), 27 pages.
Combined Chinese Office Action and Search Report issued Jul. 1, 2023 in Chinese Patent Application No. 201980079078.8 (with English Translation), 14 pages.
"Handbook of Pharmaceutical Excipients", Pharmaceutical Press and the American Pharmacists Association, 2009, pp. 1-888 (total pp. 917).
Bagirova et al., "Modern Aspects of the Use of Excipients in the technology of Drugs", Farmateca, No. 6, 1998, pp. 1-7.
Tentsova et al., "Modern biopharmaceutical aspects of excipients", Farmacya, No. 7, 2012, pp. 3-6.
Tikhonov, "Technology of Drugs: Textbook for pharmacy universities and faculties", Publishing house of NFAU, 2002, pp. 45-46 (total 3 pages).
Herkevich, "Pharmacology", Medicine, 1987, pp. 47-48, (Total 3 pages).
Unified System for Design Documentation. Types of articles. GOST 2.101 68, "Standard info", 2007, pp. 1-4.
International Search Report and Written Opinion issued Feb. 18, 2020 in PCT/EP2019/086111 filed Dec. 18, 2019.
Russian Office Action issued Sep. 20, 2023 in Russian Patent Application No. 2021122231/04 (with English Translation), 21 pages.
Japanese Office Action issued Jan. 18, 2024 in Japanese Patent Application No. 2021-537916 (with English Translation), 15 pages.

* cited by examiner

*Primary Examiner* — Robert A Wax
*Assistant Examiner* — Quanglong N Truong
(74) *Attorney, Agent, or Firm* — Oblon, McClelland, Maier & Neustadt, L.L.P.

(57) ABSTRACT

A liquid nicotine formulation for an aerosol-generating system is provided, the nicotine formulation including: one or more water-miscible polyhydric alcohols, the nicotine formulation having a water-miscible polyhydric alcohol content of greater than or equal to about 5 percent by weight; and one or more low molar mass metal salts, the one or more low molar mass metal salts being selected from the group consisting of metal cinnamates, metal cycloheptanecarboxylates, metal levulinates, metal propanoates, metal stearates, and metal undecanoates. An aerosol-generating article and an aerosol-generating system are also provided.

14 Claims, 1 Drawing Sheet

LIQUID NICOTINE FORMULATION COMPRISING LOW MOLAR MASS METAL SALT

The invention relates to a liquid nicotine formulation for use in an aerosol-generating system. The invention also relates to an aerosol-generating article comprising the liquid nicotine formulation for use in an aerosol-generating system and an aerosol-generating system comprising the liquid nicotine formulation and an atomiser.

Aerosol-generating systems for delivering nicotine to a user that comprise an atomiser configured to generate an inhalable aerosol from a liquid nicotine formulation are known. Some known aerosol-generating systems comprise a thermal atomiser such as an electric heater that is configured to heat and vaporise the liquid nicotine formulation to generate an aerosol. Other known aerosol-generating systems comprise a non-thermal atomiser that is configured to generate an aerosol from the liquid nicotine formulation using, for example, impinging jet, ultrasonic or vibrating mesh technologies. Typical liquid nicotine formulations for use in aerosol-generating systems comprise glycerine, propylene glycol and water as solvents.

It would be desirable to provide a liquid nicotine formulation that exhibits more efficient vaporization of nicotine and increased nicotine delivery to a user compared to typical liquid nicotine formulations when used in an aerosol-generating system.

It would also be desirable to provide a liquid nicotine formulation that exhibits reduced risk of leakage compared to typical liquid nicotine formulations when used in an aerosol-generating system.

According to the invention there is provided a liquid nicotine formulation for use in an aerosol-generating system, the nicotine formulation comprising: one or more water-miscible polyhydric alcohols, wherein the nicotine formulation has a water-miscible polyhydric alcohol content of greater than or equal to about 5 percent by weight; and one or more low molar mass metal salts.

According to the invention there is also provided an aerosol-generating article for use in an aerosol-generating system, the aerosol-generating article containing a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal salts.

According to the invention there is further provided an aerosol-generating system comprising: a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal salts; and an atomiser configured to generate an aerosol from the liquid nicotine formulation.

According to the invention there is also provided a liquid nicotine formulation for use in an aerosol-generating system, the nicotine formulation comprising: one or more water-miscible polyhydric alcohols, wherein the nicotine formulation has a water-miscible polyhydric alcohol content of greater than or equal to about 5 percent by weight; and one or more low molar mass metal salts, wherein the one or more low molar mass metal salts are selected from the group consisting of metal benzoates, metal cinnamates, metal cycloheptanecarboxylates, metal levulinates, metal propanoates, metal stearates and metal undecanoates.

According to the invention there is also provided an aerosol-generating article for use in an aerosol-generating system, the aerosol-generating article containing a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal salts, wherein the one or more low molar mass metal salts are selected from the group consisting of metal benzoates, metal cinnamates, metal cycloheptanecarboxylates, metal levulinates, metal propanoates, metal stearates and metal undecanoates.

According to the invention there is further provided an aerosol-generating system comprising: a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal salts; and an atomiser configured to generate an aerosol from the liquid nicotine formulation, wherein the one or more low molar mass metal salts are selected from the group consisting of metal benzoates, metal cinnamates, metal cycloheptanecarboxylates, metal levulinates, metal propanoates, metal stearates and metal undecanoates.

As used herein with reference to the invention, the term "liquid nicotine formulation" describes a liquid formulation comprising nicotine or a gel formulation comprising nicotine.

As used herein with reference to the invention, the term "gel" describes a substantially dilute cross-linked system, which exhibits no flow when in the steady-state.

As used herein with reference to the invention, the term "nicotine" describes nicotine, nicotine base or a nicotine salt. In embodiments in which the liquid nicotine formulation comprises a nicotine base or a nicotine salt, the amounts of nicotine recited herein are the amount of free base nicotine or amount of protonated nicotine, respectively.

As used herein with reference to the invention, the term "water-miscible polyhydric alcohol" describes a polyhydric alcohol that is liquid at 20° C. and mixes with water in all proportions to form a homogenous solution.

As used herein with reference to the invention, the term "low molar mass metal salt" describes a metal salt having a molar mass of less than or equal to about 500 g/mol.

Unless stated otherwise, percentages by weight of components of the liquid nicotine formulation recited herein are based on the total weight of the liquid nicotine formulation.

Bonding between the one or more low molar mass metal salts and the one or more polyhydric alcohols in the liquid nicotine formulation may elevate the boiling point of the one or more polyhydric alcohols. This may advantageously enhance vaporization of nicotine from the liquid nicotine formulation when used in an aerosol-generating system as compared to a typical liquid nicotine formulation that does not include one or more low molar mass metal salts.

Without wishing to be bound by theory, the interactions between the one or more low molar mass metal salts and the molecules of the one or more polyhydric alcohols in the liquid nicotine formulation may be stronger than the interactions between the molecules of the one or more polyhydric alcohols. This may result in more energy being required to vaporize the one or more polyhydric alcohols. In use, the inclusion of one or more low molar mass metal salts in the liquid nicotine formulation may thereby advantageously increase the percentage of nicotine in an aerosol generated from the liquid nicotine formulation by up to one order of magnitude compared to a typical liquid nicotine formulation that does not include one or more low molar mass metal salts.

Bonding between the one or more low molar mass metal salts and the one or more polyhydric alcohols in the liquid nicotine formulation may increase the viscosity of the liquid nicotine formulation compared to a typical liquid nicotine formulation that does not include one or more low molar mass metal salts. This may advantageously reduce the risk of leakage of the liquid nicotine formulation when used in an aerosol-generating system compared to a typical liquid nicotine formulation that does not include one or more low molar mass metal salts.

Including propylene glycol in the nicotine formulation may also improve vaporisation of the nicotine formulation, which can lead to the production of more aerosol for a given heating cycle.

By including propylene glycol in the nicotine formulation, there may also be an improvement in the nicotine content of the aerosol due to vaporisation of the nicotine. It is believed that this may be due to propylene glycol having a lower boiling point (188° C.) compared to glycerine (290° C.). However, if there is high amount of propylene glycol in the nicotine formulation then the nicotine content of the aerosol has been found to decrease. Therefore, it may be advantageous to have a limited amount of propylene glycol in the nicotine formulation.

The liquid nicotine formulation may have a viscosity at 25° C. of greater than or equal to about 5 Pa·s.

Preferably, the liquid nicotine formulation has a viscosity at 25° C. of greater than or equal to about 10 Pa·s. For example, the liquid nicotine formulation may have a viscosity at 25° C. of greater than or equal to about 25 Pa·s, greater than or equal to about 50 Pa·s or greater than or equal to about 75 Pa·s.

More preferably, the liquid nicotine formulation has a viscosity at 25° C. of greater than or equal to about 100 Pa·s. For example, the liquid nicotine formulation may have a viscosity at 25° C. of greater than or equal to about 250 Pa·s, greater than or equal to about 500 Pa·s or greater than or equal to about 750 Pa·s.

Most preferably, the liquid nicotine formulation has a viscosity at 25° C. of greater than or equal to about 1000 Pa·s. For example, the liquid nicotine formulation may have a viscosity at 25° C. of greater than or equal to about 2500 Pa·s, greater than or equal to about 5000 Pa·s, greater than or equal to about 7500 Pa·s or greater than or equal to about 10,000 Pa·s.

Unless stated otherwise, viscosity values recited herein are the viscosity of a 1 cubic centimetre (cm³) sample volume of liquid nicotine formulation measured using a Thermo Scientific HAAKE RheoStress 6000 rheometer using a parallel plate P20 probe with a MP60 (60 mm diameter) measuring plate at 25° C. at a speed of 6 revolutions per minute (rpm).

Liquid nicotine formulations according to the invention may advantageously be used as aerosol-forming substrates in aerosol-generating systems that comprise an automatic or manual mechanism to move or advance the aerosol-forming substrate toward the atomiser as illustrated in FIGS. 1-3. The aerosol-forming substrate thus maintains contact with the atomiser even as the aerosol-forming substrate is consumed during use. In such aerosol-generating systems, the advancement mechanism may form a portion of an aerosol-generating article comprising the liquid nicotine formulation or a portion of an aerosol-generating device that receives an aerosol-generating article comprising the liquid nicotine formulation.

The liquid nicotine formulation may comprise natural nicotine or synthetic nicotine.

The liquid nicotine formulation may have a nicotine content of greater than or equal to about 0.5 percent by weight.

Preferably, the liquid nicotine formulation has a nicotine content of greater than or equal to about 1 percent by weight. More preferably, the liquid nicotine formulation has a nicotine content of greater than or equal to about 1.5 percent by weight.

The liquid nicotine formulation may have a nicotine content of less than or equal to about 10 percent by weight or less than or equal to about 8 percent by weight.

Preferably, the liquid nicotine formulation has a nicotine content of less than or equal to about 5 percent by weight. More preferably, the liquid nicotine formulation has a nicotine content of less than or equal to about 3 percent by weight.

The liquid nicotine formulation may have a nicotine content of between about 0.5 percent by weight and about 10 percent by weight. For example, the liquid nicotine formulation may have a nicotine content of between about 0.5 percent by weight and about 8 percent by weight, between about 0.5 percent by weight and about 5 percent by weight or between about 0.5 percent by weight and about 3 percent by weight.

Preferably, the liquid nicotine formulation has a nicotine content of between about 1 percent by weight and about 10 percent by weight. For example, the liquid nicotine formulation may have a nicotine content of between about 1 percent by weight and about 8 percent by weight, between about 1 percent by weight and about 5 percent by weight or between about 1 percent by weight and about 3 percent by weight.

More preferably, the liquid nicotine formulation has a nicotine content of between about 1.5 percent by weight and about 10 percent by weight. For example, the liquid nicotine formulation may have a nicotine content of between about 1.5 percent by weight and about 8 percent by weight, between about 1.5 percent by weight and about 5 percent by weight or between about 1.5 percent by weight and about 3 percent by weight.

The liquid nicotine formulation has a water-miscible polyhydric alcohol content of greater than or equal to about 5 percent by weight.

The liquid nicotine formulation may have a water-miscible polyhydric alcohol content of greater than or equal to about 10 percent by weight, greater than or equal to about 20 percent by weight or greater than or equal to about 30 percent by weight.

Preferably, the liquid nicotine formulation has a water-miscible polyhydric alcohol content of greater than or equal to about 40 percent by weight. More preferably, the liquid nicotine formulation has a water-miscible polyhydric alcohol content of greater than or equal to about 50 percent by weight. Most preferably, the liquid nicotine formulation has a water-miscible polyhydric alcohol content of greater than or equal to about 60 percent by weight. For example, the liquid nicotine formulation may have a water-miscible polyhydric alcohol content of greater than or equal to about 70 percent by weight, greater than or equal to about 80 percent by weight or greater than or equal to about 90 percent by weight.

Preferably, the liquid nicotine formulation has a water-miscible polyhydric alcohol content of less than or equal to about 95 percent by weight.

The liquid nicotine formulation may have a water-miscible polyhydric alcohol content of between about 5 percent by weight and about 95 percent by weight. For example, the liquid nicotine formulation may have a water-miscible polyhydric alcohol content of between about 10 percent by weight and about 95 percent by weight, between about 20 percent by weight and about 95 percent by weight or between about 30 percent by weight and about 95 percent by weight.

Preferably, the liquid nicotine formulation has a water-miscible polyhydric alcohol content of between about 40 percent by weight and about 95 percent by weight. More preferably, the liquid nicotine formulation has a water-miscible polyhydric alcohol content of between about 50 percent by weight and about 95 percent by weight. Most preferably, the liquid nicotine formulation has a water-miscible polyhydric alcohol content of between about 60 percent by weight and about 95 percent by weight. For example, the liquid nicotine formulation may have a water-miscible polyhydric alcohol content of between about 70 percent by weight and about 95 percent by weight, between about 80 percent by weight and about 95 percent by weight or between about 90 percent by weight and about 95 percent by weight.

Preferably, the liquid nicotine formulation comprises one or more water-miscible polyhydric alcohols selected from the group consisting of 1,3-butanediol, glycerine, propylene glycol, and triethylene glycol.

More preferably, the liquid nicotine formulation comprises glycerine.

Most preferably, the liquid nicotine formulation comprises vegetable glycerine.

Preferably, the liquid nicotine formulation has a glycerine content of greater than or equal to about 5 percent by weight.

According to a preferred embodiment of the invention there is provided a liquid nicotine formulation for use in an aerosol-generating system, the nicotine formulation comprising: glycerine, wherein the nicotine formulation has a glycerine content of greater than or equal to about 5 percent by weight; and one or more low molar mass metal salts.

According to a preferred embodiment of the invention there is also provided an aerosol-generating article for use in an aerosol-generating system, the aerosol-generating article containing a liquid nicotine formulation comprising: glycerine, wherein the nicotine formulation has a glycerine content of greater than or equal to about 5 percent by weight; and one or more low molar mass metal salts.

According to a preferred embodiment of the invention there is further provided an aerosol-generating system comprising: a liquid nicotine formulation comprising: glycerine, wherein the nicotine formulation has a glycerine content of greater than or equal to about 5 percent by weight; and one or more low molar mass metal salts; and an atomiser configured to generate an aerosol from the liquid nicotine formulation.

The liquid nicotine formulation may have a glycerine content of greater than or equal to about 10 percent by weight, greater than or equal to about 20 percent by weight or greater than or equal to about 30 percent by weight.

Preferably, the liquid nicotine formulation has a glycerine content of greater than or equal to about 40 percent by weight. More preferably, the liquid nicotine formulation has a glycerine content of greater than or equal to about 50 percent by weight. Most preferably, the liquid nicotine formulation has a glycerine content of greater than or equal to about 60 percent by weight. For example, the liquid nicotine formulation may have a glycerine content of greater than or equal to about 70 percent by weight, greater than or equal to about 80 percent by weight or greater than or equal to about 90 percent by weight.

Preferably, the liquid nicotine formulation has a glycerine content of less than or equal to about 95 percent by weight.

The liquid nicotine formulation may have a glycerine content of between about 5 percent by weight and about 95 percent by weight. For example, the liquid nicotine formulation may have a glycerine content of between about 10 percent by weight and about 95 percent by weight, between about 20 percent by weight and about 95 percent by weight or between about 30 percent by weight and about 95 percent by weight.

Preferably, the liquid nicotine formulation has a glycerine content of between about 40 percent by weight and about 95 percent by weight. More preferably, the liquid nicotine formulation has a glycerine content of between about 50 percent by weight and about 95 percent by weight. Most preferably, the liquid nicotine formulation has a glycerine content of between about 60 percent by weight and about 95 percent by weight. For example, the liquid nicotine formulation may have a glycerine content of between about 70 percent by weight and about 95 percent by weight, between about 80 percent by weight and about 95 percent by weight or between about 90 percent by weight and about 95 percent by weight.

The liquid nicotine formulation may comprise glycerine and propylene glycol.

In embodiments in which the liquid nicotine formulation comprises glycerine and propylene glycol, preferably the ratio of the weight percent glycerine content to the weight percent propylene glycol content of the nicotine formulation is greater than or equal to about 1. More preferably, the ratio of the weight percent glycerine content to the weight percent propylene glycol content of the nicotine formulation is greater than or equal to about 1.5. For example, the ratio of the weight percent glycerine content to the weight percent propylene glycol content of the nicotine formulation may be greater than or equal to about 2, greater than or equal to about 2.5 or greater than or equal to about 3.

The liquid nicotine formulation may comprise water.

The liquid nicotine formulation may have a water content of less than or equal to about 20 percent by weight or less than or equal to about 15 percent by weight.

Preferably, the liquid nicotine formulation has a water content of less than or equal to about 10 percent by weight. For example, the liquid nicotine formulation may a water content of less than or equal to about 8 percent by weight or less than or equal to about 6 percent by weight.

In embodiments in which the liquid nicotine formulation comprises water, the liquid nicotine formulation may have a water content of greater than or equal to about 1 percent by weight. For example, the liquid nicotine formulation may have a water content of greater than or equal to about 2 percent by weight or greater than or equal to about 3 percent by weight.

The liquid nicotine formulation may have a water content of between about 1 percent by weight and about 20 percent by weight. For example, the liquid nicotine formulation may have a water content of between about 2 percent by weight and about 20 percent by weight or between about 3 percent by weight and about 20 percent by weight.

The liquid nicotine formulation may have a water content of between about 1 percent by weight and about 15 percent by weight. For example, the liquid nicotine formulation may have a water content of between about 2 percent by weight and about 15 percent by weight or between about 3 percent by weight and about 15 percent by weight.

In embodiments in which the liquid nicotine formulation comprises water, preferably the liquid nicotine formulation has a water content of between about 1 percent by weight and about 10 percent by weight. For example, the liquid nicotine formulation may have a water content of between about 2 percent by weight and about 10 percent by weight or between about 3 percent by weight and about 10 percent by weight.

The liquid nicotine formulation may have a water content of between about 1 percent by weight and about 8 percent by weight. For example, the liquid nicotine formulation may have a water content of between about 2 percent by weight and about 8 percent by weight or between about 3 percent by weight and about 8 percent by weight.

The liquid nicotine formulation may have a water content of between about 1 percent by weight and about 6 percent by weight. For example, the liquid nicotine formulation may have a water content of between about 2 percent by weight and about 6 percent by weight or between about 3 percent by weight and about 6 percent by weight.

Preferably, the liquid nicotine formulation has a low molar mass metal salt content of greater than or equal to about 0.25 percent by weight. More preferably, the liquid nicotine formulation has a low molar mass metal salt content of greater than or equal to about 0.5 percent by weight. For example, the liquid nicotine formulation may have a low molar mass metal salt content of greater than or equal to about 0.75 percent by weight or greater than or equal to about 1 percent by weight.

Preferably, the liquid nicotine formulation has a low molar mass metal salt content of less than or equal to about 15 percent by weight. More preferably, the liquid nicotine formulation has a low molar mass metal salt content of less than or equal to about 12 percent by weight. For example, the liquid nicotine formulation may have a low molar mass metal salt content of less than or equal to about 10 percent by weight.

Preferably, the liquid nicotine formulation has a low molar mass metal salt content of between about 0.25 percent by weight and about 15 percent by weight. For example, the liquid nicotine formulation may have a low molar mass metal salt content of between about 0.25 percent by weight and about 12 percent by weight or between about 0.25 percent by weight and about 10 percent by weight.

More preferably, the liquid nicotine formulation has a low molar mass metal salt content of between about 0.5 percent by weight and about 15 percent by weight. For example, the liquid nicotine formulation may have a low molar mass metal salt content of between about 0.5 percent by weight and about 12 percent by weight or between about 0.5 percent by weight and about 10 percent by weight.

The liquid nicotine formulation may have a low molar mass metal salt content of between about 0.75 percent by weight and about 15 percent by weight. For example, the liquid nicotine formulation may have a low molar mass metal salt content of between about 0.75 percent by weight and about 12 percent by weight or between about 0.75 percent by weight and about 10 percent by weight.

The liquid nicotine formulation may have a low molar mass metal salt content of between about 1 percent by weight and about 15 percent by weight. For example, the liquid nicotine formulation may have a low molar mass metal salt content of between about 1 percent by weight and about 12 percent by weight or between about 1 percent by weight and about 10 percent by weight.

The one or more low molar mass metal salts may have a molar mass of less than or equal to about 400 g/mol.

Preferably, the one or more low molar mass metal salts are one or more low molar mass non-saccharide metal salts.

According to a preferred embodiment of the invention there is provided a liquid nicotine formulation for use in an aerosol-generating system, the nicotine formulation comprising: one or more water-miscible polyhydric alcohols, wherein the nicotine formulation has a water-miscible polyhydric alcohol content of greater than or equal to about 5 percent by weight; and one or more low molar mass non-saccharide metal salts.

According to a preferred embodiment of the invention there is also provided an aerosol-generating article for use in an aerosol-generating system, the aerosol-generating article containing a liquid nicotine formulation comprising: one or more water-miscible polyhydric alcohols, wherein the nicotine formulation has a water-miscible polyhydric alcohol content of greater than or equal to about 5 percent by weight; and one or more low molar mass non-saccharide metal salts.

According to a preferred embodiment of the invention there is further provided an aerosol-generating system comprising: a liquid nicotine formulation comprising: one or more water-miscible polyhydric alcohols, wherein the nicotine formulation has a water-miscible polyhydric alcohol content of greater than or equal to about 5 percent by weight; and one or more low molar mass non-saccharide metal salts; and an atomiser configured to generate an aerosol from the liquid nicotine formulation.

More preferably, the one or more low molar mass metal salts are one or more low molar mass metal salts selected from the group consisting of metal benzoates, metal cinnamates, metal cycloheptanecarboxylates, metal levulinates, metal propanoates, metal stearates and metal undecanoates.

In some embodiments the one or more low molar mass metal salts are one or more low molar mass metal salts selected from the group consisting of metal cinnamates, metal cycloheptanecarboxylates, metal stearates and metal undecanoates.

According to a preferred embodiment of the invention there is provided a liquid nicotine formulation for use in an aerosol-generating system, the nicotine formulation comprising: one or more water-miscible polyhydric alcohols, wherein the nicotine formulation has a water-miscible polyhydric alcohol content of greater than or equal to about 5 percent by weight; and one or more low molar mass metal salts selected from the group consisting of metal benzoates, metal cinnamates, metal cycloheptanecarboxylates metal levulinates, metal propanoates, metal stearates and metal undecanoates.

According to a preferred embodiment of the invention there is also provided an aerosol-generating article for use in an aerosol-generating system, the aerosol-generating article containing a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal salts selected from the group consisting of metal benzoates, metal cinnamates, metal cycloheptanecarboxylates, metal levulinates, metal propanoates, metal stearates and metal undecanoates.

According to a preferred embodiment of the invention there is further provided an aerosol-generating system comprising: a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal salts selected from the group consisting of metal benzoates, metal cinnamates, metal cycloheptanecarboxylates, metal levulinates, metal propanoates, metal stearates and metal undecanoates; and an atomiser configured to generate an aerosol from the liquid nicotine formulation.

Most preferably, the liquid nicotine formulation comprises one or more low molar mass metal stearates.

Advantageously, covalent bonding between the one or more metal stearates and the one or more water-miscible polyhydric alcohols in the nicotine formulation may further elevate the boiling point of the one or more water-miscible polyhydric alcohols. When the formulation includes nicotine, this may advantageously enhance the efficiency of vaporization of nicotine from the nicotine formulation when used in an aerosol-generating system as compared to a typical liquid nicotine formulation that does not include one or more metal stearates.

According to a preferred embodiment of the invention there is provided a liquid nicotine formulation for use in an aerosol-generating system, the nicotine formulation comprising: one or more water-miscible polyhydric alcohols, wherein the nicotine formulation has a water-miscible polyhydric alcohol content of greater than or equal to about 5 percent by weight; and one or more low molar mass metal stearates.

According to a preferred embodiment of the invention there is also provided an aerosol-generating article for use in an aerosol-generating system, the aerosol-generating article containing a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal stearates.

According to a preferred embodiment of the invention there is further provided an aerosol-generating system comprising: a liquid nicotine formulation comprising: one or more water-miscible polyhydric alcohols, wherein the nicotine formulation has a water-miscible polyhydric alcohol content of greater than or equal to about 5 percent by weight; and one or more low molar mass metal stearates; and an atomiser configured to generate an aerosol from the liquid nicotine formulation.

Particularly preferably, the liquid nicotine formulation comprises glycerine and one or more low molar mass metal stearates.

Covalent bonding between the one or more low molar mass metal stearates and the glycerine in the liquid nicotine formulation may elevate the boiling point of the glycerine. This may advantageously enhance vaporization of nicotine from the liquid nicotine formulation when used in an aerosol-generating system.

Covalent bonding between the one or more low molar mass metal stearates and the glycerine in the liquid nicotine formulation may increase the viscosity of the liquid nicotine formulation. This may advantageously reduce the risk of leakage of the liquid nicotine formulation when used in an aerosol-generating system.

The liquid nicotine formulation may comprise one or more low molar mass salts of any suitable metal.

Preferably, the liquid nicotine formulation comprises one or more low molar mass alkali metal salts.

More preferably, the liquid nicotine formulation comprises one or more low molar mass sodium salts.

Preferably, the liquid nicotine formulation comprises one or more low molar mass non-saccharide sodium salts.

More preferably, the liquid nicotine formulation comprises one or more sodium salts selected from the group consisting of sodium benzoate, sodium cinnamate, sodium cycloheptanecarboxylate, sodium levulinate, sodium propanoate, sodium stearate and sodium undecanoate.

Most preferably, the liquid nicotine formulation comprises sodium stearate.

A metal salt with a high weighted average molecular weight may improve the above mentioned advantages related to efficiency of vaporization of nicotine. However, if the weighted average molecular weight of a metal salt is too high then properties such as solubility begin to be negatively affected. Advantageously, including sodium stearate in the formulation may provide an optimal trade-off in improved efficiency of vaporization of nicotine, whilst maintaining solubility.

According to a preferred embodiment of the invention there is provided a liquid nicotine formulation for use in an aerosol-generating system, the nicotine formulation comprising: one or more water-miscible polyhydric alcohols, wherein the nicotine formulation has a water-miscible polyhydric alcohol content of greater than or equal to about 5 percent by weight; and sodium stearate.

According to a preferred embodiment of the invention there is also provided an aerosol-generating article for use in an aerosol-generating system, the aerosol-generating article containing a liquid nicotine formulation comprising: one or more water-miscible polyhydric alcohols, wherein the nicotine formulation has a water-miscible polyhydric alcohol content of greater than or equal to about 5 percent by weight; and sodium stearate.

According to a preferred embodiment of the invention there is further provided an aerosol-generating system comprising: a liquid nicotine formulation comprising: one or more water-miscible polyhydric alcohols, wherein the nicotine formulation has a water-miscible polyhydric alcohol content of greater than or equal to about 5 percent by weight; and sodium stearate; and an atomiser configured to generate an aerosol from the liquid nicotine formulation.

In embodiments in which the liquid nicotine formulation comprises sodium stearate, preferably the liquid nicotine formulation has a sodium stearate content of greater than or equal to about 0.25 percent by weight. More preferably, the liquid nicotine formulation has a sodium stearate content of greater than or equal to about 0.5 percent by weight. For example, the liquid nicotine formulation may have a sodium stearate content of greater than or equal to about 0.75 percent by weight or greater than or equal to about 1 percent by weight.

Preferably, the liquid nicotine formulation has a sodium stearate content of less than or equal to about 15 percent by weight. More preferably, the liquid nicotine formulation has a sodium stearate content of less than or equal to about 12 percent by weight. For example, the liquid nicotine formulation may have a sodium stearate content of less than or equal to about 10 percent by weight.

Preferably, the liquid nicotine formulation has a sodium stearate content of between about 0.25 percent by weight and about 15 percent by weight. For example, the liquid nicotine formulation may have a sodium stearate content of between about 0.25 percent by weight and about 12 percent by weight or between about 0.25 percent by weight and about 10 percent by weight.

More preferably, the liquid nicotine formulation has a sodium stearate content of between about 0.5 percent by weight and about 15 percent by weight. For example, the liquid nicotine formulation may have a sodium stearate content of between about 0.5 percent by weight and about 12 percent by weight or between about 0.5 percent by weight and about 10 percent by weight.

The liquid nicotine formulation may have a sodium stearate content of between about 0.75 percent by weight and about 15 percent by weight. For example, the liquid nicotine formulation may have a sodium stearate content of between about 0.75 percent by weight and about 12 percent by weight or between about 0.75 percent by weight and about 10 percent by weight.

The liquid nicotine formulation may have a sodium stearate content of between about 1 percent by weight and about 15 percent by weight. For example, the liquid nicotine formulation may have a sodium stearate content of between about 1 percent by weight and about 12 percent by weight or between about 1 percent by weight and about 10 percent by weight.

Particularly preferably, the liquid nicotine formulation comprises glycerine and sodium stearate.

According to a particularly preferred embodiment of the invention there is provided a liquid nicotine formulation for use in an aerosol-generating system, the nicotine formulation comprising: glycerine, wherein the nicotine formulation has a glycerine content of greater than or equal to about 5 percent by weight; and sodium stearate.

According to a particularly preferred embodiment of the invention there is also provided an aerosol-generating article for use in an aerosol-generating system, the aerosol-generating article containing a liquid nicotine formulation comprising: glycerine, wherein the nicotine formulation has a glycerine content of greater than or equal to about 5 percent by weight; and sodium stearate.

According to a preferred embodiment of the invention there is further provided an aerosol-generating system comprising: a liquid nicotine formulation comprising: glycerine, wherein the nicotine formulation has a glycerine content of greater than or equal to about 5 percent by weight; and sodium stearate; and an atomiser configured to generate an aerosol from the liquid nicotine formulation.

Covalent bonding between the sodium stearate and the glycerine in the liquid nicotine formulation may elevate the boiling point of the glycerine. This may advantageously enhance vaporization of nicotine from the liquid nicotine formulation when used in an aerosol-generating system.

Covalent bonding between the sodium stearate and the glycerine in the liquid nicotine formulation may increase the viscosity of the liquid nicotine formulation. This may advantageously reduce the risk of leakage of the liquid nicotine formulation when used in an aerosol-generating system.

The liquid nicotine formulation may comprise one or more organic acids.

In some embodiments the one or more organic acids may be water-soluble organic acids. As used herein with reference to the invention, the term "water-soluble organic acid" describes an organic acid having a water solubility at 20° C. of greater than or equal to about 100 mg/ml, preferably greater than or equal to about 500 mg/ml, more preferably greater than or equal to about 750 mg/ml most preferably greater than or equal to about 1000 mg/ml.

Unless stated otherwise, water solubility values recited herein are the water solubility measured based on the preliminary test of OECD (1995), *Test No. 105: Water Solubility*, OECD Guidelines for the Testing of Chemicals, Section 1, OECD Publishing, Paris, https://doi.org/10.1787/9789264069589-en. In a stepwise procedure, increasing volumes of distilled water are added at 20° C. to 0.1 g of the sample (solid substances must be pulverized) in a 10 ml glass-stoppered measuring cylinder. However, when the substance is an acid, the sample is added to the distilled water in the first step. After each addition of an amount of water, the mixture is shaken for 10 minutes and is visually checked for any undissolved parts of the sample. If, after addition of 10 ml of water, the sample or parts of it remain undissolved, the experiment is continued in a 100 ml measuring cylinder. The approximate solubility is given in Table 1 below under that volume of water in which complete dissolution of the sample occurs.

When the solubility is low, a long time may be required to dissolve a substance and at least 24 hours should be allowed. If, after 24 hours, the substance is still not dissolved, the measuring cylinder is placed for at 40° C. in an ultrasound bath for 15 minutes and another 24 hours allowed (up to a maximum of 96 hours). If the substance is still not dissolved, the solubility is considered to be below the limit value or not soluble.

TABLE 1

| ml of water in which 0.1 g of sample is soluble | 0.1 | 0.5 | 1 | 2 | 10 | 100 | >100 |
|---|---|---|---|---|---|---|---|
| Approximate solubility (mg/ml) | >1000 | 1000 to 200 | 200 to 100 | 100 to 50 | 50 to 10 | 10 to 1 | <1 |

The liquid nicotine formulation may comprise one or more carboxylic acids.

Suitable carboxylic acids include, but are not limited to, acetic acid, citric acid, lactic acid, malic acid, malonic acid and pyruvic acid.

In embodiments in which the nicotine formulation comprises one or more organic acids, the liquid nicotine formulation may have an organic acid content of greater than or equal to about 0.5 percent by weight or greater than or equal to about 1 percent by weight.

Preferably, the liquid nicotine formulation has an organic acid content of less than or equal to about 6 percent by weight. More preferably, the liquid nicotine formulation has an organic acid content of less than or equal to about 4 percent by weight. For example, the liquid nicotine formulation may an organic acid content of less than or equal to about 2 percent by weight.

The liquid nicotine formulation may have an organic acid content of between about 0.5 percent by weight and about 6 percent by weight. For example, the liquid nicotine formulation may have an organic acid content of between about 0.5 percent by weight and about 4 percent by weight or between about 0.5 percent by weight and about 2 percent by weight.

In embodiments in which the nicotine formulation comprises one or more organic acids, the liquid nicotine formulation may have an organic acid content of between about 1 percent by weight and about 6 percent by weight. For example, the liquid nicotine formulation may have an organic acid content of between about 1 percent by weight and about 4 percent by weight or between about 1 percent by weight and about 2 percent by weight.

The liquid nicotine formulation may comprise one or more flavourants. Suitable flavourants include, but are not limited to, menthol.

Preferably, the liquid nicotine formulation has a flavourant content of less than or equal to about 4 percent by weight. More preferably, the liquid nicotine formulation has a flavourant content of less than or equal to about 3 percent by weight.

According to the invention there is also provided an aerosol-generating article for use in an aerosol-generating system, the aerosol-generating article containing a liquid nicotine formulation according to the invention.

The aerosol-generating article may comprise an atomiser configured to generate an aerosol from the liquid nicotine formulation.

The aerosol-generating article may be a cartridge.

A cartridge containing the liquid nicotine formulation and an atomiser may be referred to as a "cartomiser".

The atomiser may be a thermal atomiser.

As used herein with reference to the invention, the term "thermal atomiser" describes an atomiser that is configured to heat the liquid nicotine formulation to generate an aerosol.

The aerosol-generating article may comprise any suitable type of thermal atomiser.

The thermal atomiser may comprise an electric heater. For example, the thermal atomiser may comprise an electric heater comprising a resistive heating element or an inductive heating element.

The heating element may be a grid or mesh element or layer. In such embodiments, the liquid nicotine formulation may flow into the interstitial spaces forming the grid or mesh element.

The atomiser may be a non-thermal atomiser.

As used herein with reference to the invention, the term "non-thermal atomiser" describes an atomiser that is configured to generate an aerosol from the liquid nicotine formulation by means other than heating.

The aerosol-generating article may comprise any suitable type of non-thermal atomiser.

For example, the non-thermal atomiser may be an impinging jet atomiser, an ultrasonic atomiser or a vibrating mesh atomiser.

According to the invention there is further provided an aerosol-generating system comprising a liquid nicotine formulation according to the invention and an atomiser configured to generate an aerosol from the liquid nicotine formulation.

The atomiser may be a thermal atomiser.

The aerosol-generating system may comprise any suitable type of thermal atomiser.

The thermal atomiser may comprise an electric heater. For example, the thermal atomiser may comprise an electric heater comprising a resistive heating element or an inductive heating element.

The heating element may be a grid or mesh element or layer. In such embodiments, the liquid nicotine formulation may flow into the interstitial spaces forming the grid or mesh element.

The atomiser may be a non-thermal atomiser.

The aerosol-generating system may comprise any suitable type of non-thermal atomiser.

For example, the non-thermal atomiser may be an impinging jet atomiser, an ultrasonic atomiser or a vibrating mesh atomiser.

The aerosol-generating system may comprise: an aerosol-generating article according to the invention containing the liquid nicotine formulation and an aerosol-generating device comprising a housing defining a device cavity configured to receive at least a portion of the aerosol-generating article.

The aerosol-generating system may comprise a consumable aerosol-generating article according to the invention containing the liquid nicotine formulation and a reusable aerosol-generating device comprising a housing defining a device cavity configured to receive at least a portion of the aerosol-generating article.

The aerosol-generating device may comprise a battery and control electronics.

The aerosol-generating system may comprise: an aerosol-generating article according to the invention containing the liquid nicotine formulation and the atomiser; and an aerosol-generating device comprising a housing defining a device cavity configured to receive at least a portion of the aerosol-generating article.

The aerosol-generating system may comprise: an aerosol-generating article according to the invention containing the liquid nicotine formulation; and an aerosol-generating device comprising a housing defining a device cavity configured to receive at least a portion of the aerosol-generating article and the atomiser.

For the avoidance of doubt, features described above in relation to one aspect of the invention may also be applicable to other aspects of the invention. In particular, features described above in relation to the liquid nicotine formulation of the invention may also relate, where appropriate, to the aerosol-generating article of the invention and the aerosol-generating system. Similarly, features described above in relation to the aerosol-generating article of the invention may also relate, where appropriate, to the aerosol-generating system of the invention, and vice versa.

Embodiments of the invention will now be described, by way of example only, with reference to the following examples and accompanying drawings, in which.

Figure 1:
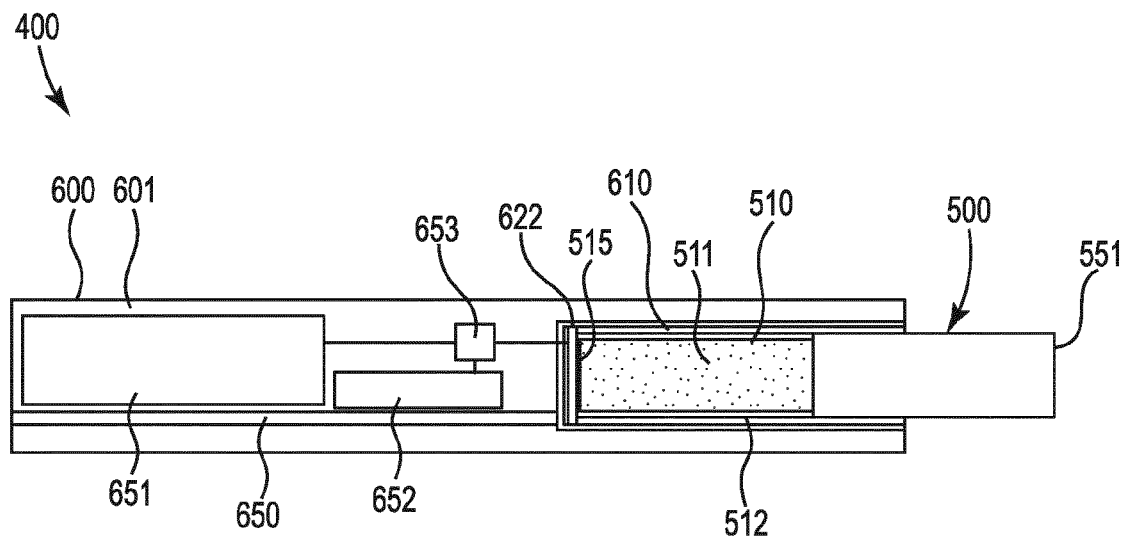
FIG. 1 is a schematic cross-sectional side view of an aerosol-generating system comprising an aerosol-generating device and an aerosol-generating article comprising a liquid nicotine formulation according to the invention.

FIG. 1 shows an aerosol-generating system 400 comprising an aerosol-generating device 600 and an aerosol-generating article 500.

The aerosol-generating device 600 shown in FIG. 1 is configured for receiving the aerosol-generating article 500. The aerosol-generating device 600 comprises a housing 601 and a receptacle 610 formed in the housing 601. The receptacle 610 is constructed for receiving the aerosol-generating article 500. The receptacle 610 may be sized and shaped so that when the aerosol-generating article 500 is inserted in the receptacle 610, at least a portion of the aerosol-generating article 500 remains outside of the receptacle 610.

The aerosol-generating device 600 comprises a heating element 622 at the closed end of the receptacle 610. The heating element 622 comprises a mesh layer.

The aerosol-generating device 600 may include a power supply 651 operably connected to a controller 653 and optional graphical user interface 652. The power supply 651 operably connected to a controller 653 may be disposed within the housing 601. The graphical user interface 652 may be disposed on the housing 601.

The aerosol-generating article 500 includes a body 512 defining a cavity 512 having a cavity opening 515. An aerosol-forming substrate 511 is disposed in the cavity 510. The body 512 includes a closed end portion 551 that may be a ring or rotation portion or a fixed support.

Alternatively, the aerosol-generating article 500 may include an advancement mechanism may be arranged in the proximal end of the aerosol-generating article 500. The advancement mechanism may be configured as a piston-type element. The advancement mechanism may be configured as a screw-type element. The advancement mechanism may translate rotational movement into lateral movement.

The cavity opening of the aerosol-generating article 500 abuts the heating element 622 when the aerosol-generating article 500 is received into the receptacle 610 of the aerosol-generating device 600. The heating element 622 is disposed proximate to the cavity opening 515. The aerosol-forming substrate 511 of the aerosol-generating article 500 is a liquid nicotine formulation according to the invention that may flow into and through the mesh layer of the heating element 622.

Air may flow into the receptacle 610 aerosol-generating device 600 and entrain the volatized aerosol components from the heated aerosol-forming substrate 511 and through the aerosol-generating device 600 via an air channel 650 and to the consumer.

Figures 2, 3:
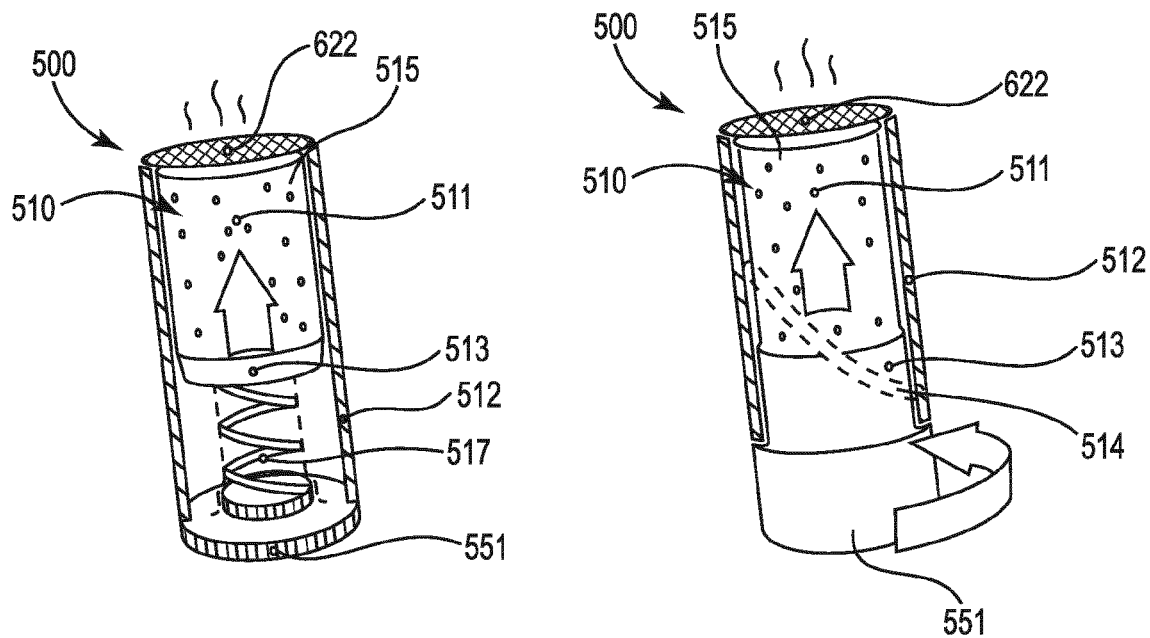
FIG. 2 is a schematic sectional view of a spring-loaded aerosol-generating article comprising a liquid nicotine formulation according to the invention.
FIG. 3 is a schematic sectional view of a "lip-stick" advance mechanism aerosol-generating article comprising a liquid nicotine formulation according to the invention.

FIG. 2 is a schematic sectional view of a spring-loaded aerosol-generating article 500. The aerosol-generating article 500 includes a body 512 defining a cavity 510 having a cavity opening 515. The aerosol-forming substrate 511 is disposed in the cavity 512. The heating element 622 is disposed proximate to the cavity opening 515. The body 512 includes a closed end portion 551 that may be a fixed support. A spring element 517 biases a movable rigid base 513 to the spring support 551 fixed to the body 512. The aerosol-forming substrate 511 is a liquid nicotine formulation according to the invention that may flow into and through the mesh layer of the heating element 622.

FIG. 3 is a schematic sectional view of a "lip-stick" advance mechanism aerosol-generating article 500. The aerosol-generating article 500 includes a body 512 defining a cavity 510 having a cavity opening 515. The aerosol-forming substrate 511 is disposed in the cavity 512. The heating element 622 is disposed proximate to the cavity opening 515. The body 512 includes a ring or rotation element 551 that is coupled to the movable rigid base 513 and translates rotational movement into lateral movement via a spiral or helical groove 514. Pins (not shown) couple the rigid base 513 to the spiral or helical groove 514 to provide the lateral movement of the aerosol-forming substrate 511. The aerosol-forming substrate 511 is a liquid nicotine formulation according to the invention that may flow into and through the mesh layer of the heating element 622.

In alternative embodiments (not shown), the aerosol-generating system may comprise an automatic mechanism to move or advance the aerosol-forming substrate 511 toward the heating element 622. In such alternative embodiments, the controller 653 of the aerosol-generating device 600 may activate an actuator or advancement mechanism on either the aerosol-generating article 500 or the aerosol-generating device 600 to advance the aerosol-forming substrate 511 and rigid base 513 toward the heating element 622 upon detecting that the heating element 622 is not in contact the aerosol-forming substrate 511.

EXAMPLES

Three liquid nicotine formulations according to the invention (Examples A, B and C) were prepared having the compositions and viscosities shown in Table 2.

TABLE 2

| Example | | A | B | C |
|---|---|---|---|---|
| Nicotine (% by weight) | | 2 | 2 | 2 |
| Water (% by weight) | | 6 | 6 | 6 |
| Vegetable Glycerine (% by weight) | polyhydric alcohol | 91 | 68 | 91.5 |
| Propylene Glycol (% by weight) | polyhydric alcohol | 0 | 23 | 0 |
| Sodium Stearate (% by weight) | low molar mass metal salt | 1 | 1 | 0.5 |
| Viscosity (Pa s) | | 3366 | 225 | 185 |

Each of the three liquid nicotine compositions was prepared by:
(1) heating the one or more polyhydric alcohols to a temperature of between about 100° C. and about 120° C. using a hotplate stirrer;
(2) adding a fine powder of the low molar mass metal salt to the one or more polyhydric alcohols, while stirring constantly, and then continuing to heat the mixture to a temperature of between about 85° C. and about 95° C. until the mixture was clear;
(3) adding water to the clear mixture;
(4) decreasing the heating temperature of the mixture to about 50° C. and adding nicotine to the mixture, while stirring constantly; and
(5) pouring the heated mixture into a mold and then allowing the mixture to cool and congeal to form the liquid nicotine composition.

As shown in Table 2, inclusion of less than or equal to about 1 percent by weight of low molar mass metal salt (sodium stearate) results in the liquid nicotine formulations having a viscosity at 25° C. of greater than or equal to about 185 Pa s.

The invention claimed is:

1. A liquid nicotine formulation for an aerosol-generating system, the liquid nicotine formulation comprising:
    nicotine;
    one or more water-miscible polyhydric alcohols, wherein the liquid nicotine formulation has a water-miscible polyhydric alcohol content of greater than or equal to about 5 percent by weight; and
    one or more low molar mass metal salts, wherein the one or more low molar mass metal salts are selected from the group consisting of metal cinnamates, metal cycloheptanecarboxylates, metal levulinates, metal propanoates, metal stearates, and metal undecanoates.

2. The liquid nicotine formulation according to claim 1, wherein the one or more low molar mass metal salts are one or more low molar mass non-saccharide metal salts.

3. The liquid nicotine formulation according to claim 1, wherein the one or more low molar mass metal salts are sodium stearate.

4. The liquid nicotine formulation according to claim 1, wherein the liquid nicotine formulation has a low molar mass metal salt content of between about 0.5 percent and about 15 percent by weight.

5. The liquid nicotine formulation according to claim 1, wherein the liquid nicotine formulation has a water-miscible polyhydric alcohol content of at least about 60 percent by weight.

6. The liquid nicotine formulation according to claim 1, wherein the one or more water-miscible polyhydric alcohols comprise glycerine.

7. The liquid nicotine formulation according to claim 6, wherein the one or more water-miscible polyhydric alcohols comprise glycerine and propylene glycol.

8. The liquid nicotine formulation according to claim 7, wherein a ratio of the weight percent glycerine content to the weight percent propylene glycol content of the liquid nicotine formulation is greater than or equal to about 1.

9. The liquid nicotine formulation according to claim 1, further comprising water.

10. The liquid nicotine formulation according to claim 3, wherein the liquid nicotine formulation has a water content of less than or equal to about 10 percent by weight.

11. The liquid nicotine formulation according to claim 1, further comprising one or more organic acids, wherein the liquid nicotine formulation has an organic acid content of between about 0.5 percent and about 4 percent by weight.

12. The liquid nicotine formulation according to claim 1, wherein the liquid nicotine formulation has a viscosity at 25° C. of greater than or equal to about 10 Pa·s.

13. An aerosol-generating article for an aerosol-generating system, the aerosol-generating article containing the liquid nicotine formulation according to claim 1.

14. An aerosol-generating system, comprising:

the liquid nicotine formulation according to claim 1; and an atomiser configured to generate an aerosol from the liquid nicotine formulation.

* * * * *